United States Patent [19]

Schurter et al.

[11] Patent Number: 4,632,695
[45] Date of Patent: Dec. 30, 1986

[54] N-PHENYLSULFONYL-N'-TRIAZINYLUREAS AS HERBICIDES AND PLANT GROWTH REGULANTS

[75] Inventors: Rolf Schurter, Binningen; Rudolph C. Thummel, Courgenay; Werner Töpfl, Dornach; Willy Meyer, Riehen; Dieter Dürr, Bottmingen, all of Switzerland

[73] Assignee: Ciba-Geigy Corporation, Ardsley, N.Y.

[21] Appl. No.: 806,168

[22] Filed: Dec. 6, 1985

Related U.S. Application Data

[63] Continuation of Ser. No. 717,638, Mar. 29, 1985, abandoned, which is a continuation-in-part of Ser. No. 574,421, Jan. 27, 1984, abandoned.

[30] Foreign Application Priority Data

Feb. 4, 1983 [CH] Switzerland .................. 643/83-2

[51] Int. Cl.⁴ ................. C07D 251/46; C07D 251/52; A01N 43/70; A01N 43/66
[52] U.S. Cl. ......................... 71/93; 544/211; 544/212; 544/206; 544/207; 544/208; 544/209; 544/3; 544/5; 544/113; 540/488; 540/524
[58] Field of Search .............. 71/93; 544/113, 211, 544/212, 206, 207, 208, 209, 315; 260/293.3

[56] References Cited

U.S. PATENT DOCUMENTS 422,533 9/1980 Levitt ........................ 71/93
4,435,205 3/1984 Reap ........................ 71/93

Primary Examiner—John M. Ford
Attorney, Agent, or Firm—Edward McC. Roberts

[57] ABSTRACT

N-Phenylsulfonyl-N'-triazinylureas of the general formula I

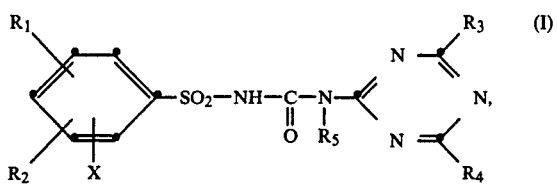

and the salts of these compounds with amines, alkali metal bases or alkaline earth metal bases or with quaternary ammonium bases, have good selective herbicidal and growth regulating properties when applied pre- and postemergence. The symbols in formula I have the following meanings:

$R_1$ is hydrogen, halogen, nitro, cyano, or an alkyl, alkoxy, alkylthio, alkylsulfonyl, alkylcarbonyl, alkylcarbamoyl or alkoxycarbonyl group, each unsubstituted or substituted by halogen or alkoxy, $R_2$ is hydrogen, halogen, alkyl, or an alkyl, alkoxy or alkylthio group, each unsubstituted or substituted by halogen or alkoxy, $R_3$ is alkyl, haloalkyl, alkoxy or haloalkoxy, $R_4$ is hydrogen, halogen, $R_3$, alkylamino or dialkylamino, $R_5$ is hydrogen, alkyl or alkoxy, and X is an alkenylamino, cycloalkylamino or cycloalkenylamino group which may be further substituted, or is a carbamoylamido or sulfonylamino group as defined in the description, or is a 5- or 6-membered saturated heterocyclic ring system which is bonded through the nitrogen atom and which may contain a further oxygen, sulfur or nitrogen atom in the ring and must contain at least one oxo group.

14 Claims, No Drawings

N-PHENYLSULFONYL-N'-TRIAZINYLUREAS AS HERBICIDES AND PLANT GROWTH REGULANTS

This is a continuation of application Ser. No. 717,638 filed on Mar. 29, 1985, now abandoned, which in turn is a continuation-in-part of application Ser. No. 574,421, filed Jan. 27, 1984, now abandoned.

The present invention relates to novel N-phenylsulfonyl-N'-triazinylureas with herbicidal and growth regulating properties, to the preparation thereof, to compositions containing them, and to the use thereof for controlling weeds, especially selectively, in crops of useful plants, or for regulating and inhibiting plant growth. The invention also relates to novel phenylsulfonamides obtained as intermediates.

The N-phenylsulfonyl-N'-triazinylureas of the present invention, and salts thereof, have the general formula I

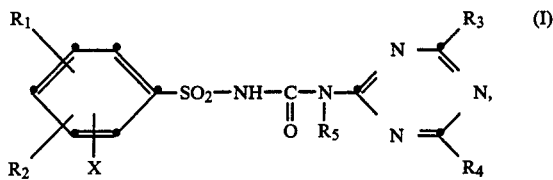

wherein
$R_1$ is hydrogen, halogen, or $COOC_1$-$C_5$alkyl
$R_2$ is hydrogen or halogen,
$R_3$ is $C_1$-$C_3$alkyl, $C_1$-$C_3$haloalkyl, $C_1$-$C_3$alkoxy, $C_1$-$C_3$haloalkoxy,
$R_4$ is hydrogen, halogen, $C_1$-$C_3$alkyl, $C_1$-$C_3$haloalkyl, $C_1$-$C_3$alkoxy, $C_1$-$C_3$haloalkoxy, $C_2$-$C_4$alkoxyalkyl or an amino, $C_1$-$C_3$alkyl- or di-$C_1$-$C_3$alkylamino group,
$R_5$ is hydrogen or methyl
X is a $-NR_6R_7$, $-NHSO_2CH_3$, $-N(SO_2CH_3)_2$ or

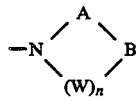

A is a $-CO-$ or $-SO_2-$ group,
B is a $C_1$-$C_4$alkylene or $C_2$-$C_4$alkenylene group,
W is $-CO-$ or $-SO_2-$,
n is 0 or 1,
$R_6$ is $C_2$-$C_6$alkenyl, $C_3$-$C_7$cycloalkyl, $C_5$-$C_7$cycloalkenyl, unsubstituted, or substituted by halogen, cyano, or a $-COOR_{11}$ group; or it is a $-COR_8$, $-CONR_9R_{10}$ or a $-COCOOR_{11}$ rest,
$R_7$ is hydrogen, $C_1$-$C_4$alkyl, $C_3$-$C_7$cycloalkyl or the $-SO_2CH_3$ group,
$R_8$ is hydrogen, $C_1$-$C_5$alkyl, $C_3$-$C_7$cycloalkyl, $C_1$-$C_5$haloalkyl or $C_2$-$C_5$alkoxyalkyl,
$R_9$ is hydrogen or $C_1$-$C_4$alkyl.
$R_{10}$ is hydrogen, $C_1$-$C_5$haloalkyl or $C_2$-$C_6$alkenyl,
$R_{11}$ is hydrogen, $C_1$-$C_5$haloalkyl, $C_2$-$C_5$alkoxyalkyl, $C_2$-$C_6$alkenyl, $C_2$-$C_4$haloalkenyl or $C_2$-$C_4$alkynyl.

Herbicidally active ureas, triazines and pyrimidines are generally known in the art. Arylsulfoamoyl-heterocyclyl-aminocarbamoyl compounds with herbicidal and plant growth regulating properties have been described e.g. in Netherlands Patent Specification No. 121 788 or in European patent application No. 44 210.

In the above definitions, alkyl denotes straight chain or branched alkyl and is e.g.: methyl, ethyl, n-propyl, isopropyl, the 4 isomers of butyl, n-amyl, isoamyl, 2-amyl, 3-amyl, n-hexyl, isohexyl, or the different isomers of heptyl, octyl or nonyl.

Alkoxy is e.g.: methoxy, ethoxy, n-propoxy, isopropoxy and the 4-isomers of butoxy, with methoxy, ethoxy or isopropoxy being preferred.

Alkylthio is e.g. methylthio, ethylthio, n-propylthio, isopropylthio and n-butylthio, with methylthio and ethylthio being preferred.

Examples of alkenyl radicals are: vinyl, allyl, isopropenyl, 1-propenyl, 1-butenyl, 2-butenyl, 3-butenyl, 1-isobutenyl, 2-isobutenyl, 1-pentenyl, 2-pentenyl, 3-pentenyl and 4-pentenyl, with vinyl, allyl and 4-pentenyl being preferred.

Halogen in the above definitions, and also as moiety of haloalkyl, haloalkoxy and haloalkylthio, is fluorine, chlorine and bromine, with fluorine and chlorine being preferred.

Alkynyl in the above definitions is as a rule propargyl, 2-butynyl, 3-butynyl, and also the isomers of pentynyl or hexynyl. The preferred alkynyl radical, however, is propargyl or 2- or 3-butynyl.

The group

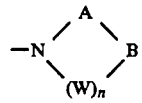

represents preferably a 5- to 6-membered heterocyclic ring, which is saturated or unsaturated and contains 1 to 2 $-CO-$ or $-SO_2-$ groups, such as e.g. pyrrolidinon, pyrrolidindion, 1,1-dioxo-isothiazolin, imidazolidinon, piperidinon, oxazolidinon, morpholinon or 1,1-dioxothiomorpholinon rings.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four isomers of butylamine, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Especially good herbicidal and plant-growth regulatory activity has been observed with those compounds of formula I, wherein the radicals $R_3$ and $R_4$ together contain not more than 4 carbon atoms, and further with the compounds of the formula wherein $R_1$ is hydrogen, halogen or $C_1$-$C_5$alkoxycarbonyl,
$R_2$ is hydrogen,
$R_3$ is $C_1$-$C_3$alkyl, $C_1$-$C_3$-haloalkyl, $C_1$-$C_3$alkoxy or $C_1$-$C_3$haloalkoxy,
$R_4$ is hydrogen, halogen or has the same meaning as $R_3$ or is $C_1$-$C_4$alkyl or dialkylamino,
$R_5$ is hydrogen or methyl,
X is a —$NH_6R_7$ or

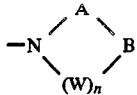

$R_6$ is $C_2$-$C_6$alkenyl, $C_3$-$C_7$cycloalkyl, $C_5$-$C_7$cycloalkenyl, unsubstituted, or substituted by halogen, cyano, —CO—$C_1$-$C_5$alkyl, —COO—$C_1$-$C_5$alkyl, or is a —CO—$C_1$-$C_5$haloalkyl, —CO—$C_2$-$C_{10}$alkoxyalkyl, —CO—$C_3$-$C_7$cycloalkyl, or —COCOO—$C_1$-$C_5$alkyl group, $R_7$ is hydrogen, $C_1$-$C_5$alkyl, $C_3$-$C_7$cycloalkyl or is —$SO_2CH_3$, A is —CO— or —$SO_2$—,
B is $C_{1-4}$alkylene or $C_2$-$C_4$alkenylene,
W is —CO— or —$SO_2$— and
n is 0 or 1.

Good activity have also shown the compounds of the formula I, wherein $R_1$ is hydrogen or halogen
$R_2$ is hydrogen,
$R_3$ is $C_1$-$C_3$alkyl, $C_1$-$C_3$haloalkyl, $C_1$-$C_3$alkoxy or $C_1$-$C_4$haloalkoxy,
$R_4$ is hydrogen, halogen, or has the same meaning as $R_3$ or is di($C_1$-$C_3$)alkylamine,
$R_5$ is hydrogen,
X is —NH—$C_2$-$C_5$alkenyl, —NH—$C_3$-$C_7$cycloalkyl or —NH—$C_5$-$C_7$cycloalkenyl, unsubstituted or substituted by halogen, cyano, —CO—$C_1$-$C_5$haloalkyl, —CO—$C_2$-$C_6$alkoxyalkyl or —COO—$C_1$-$C_5$alkyl; and it is also —NHCHO, —NHCO—$C_1$-$C_5$haloalkyl, —NHCOO—$C_1$-$C_5$haloalkyl, —NHCONH—$C_1$-$C_5$-haloalkyl, —NHCOCOO—$C_1$-$C_5$alkyl, —NH-$SO_2$-$CH_3$, —N($SO_2$-$CH_3$)$_2$; or is a pyrrolidinone, 1,1-dioxo-isothiazolidine, piperidinone, pyrrolidinone, pyrrolidindione or oxazolidinone ring.

Preferred individual compounds are:
N-(2-trifluoroacetamidophenylsulfonyl)-N'-(4-methoxy-6-methyl-1,3,5-triazin-2-yl)urea,
N-[2-(2',2'-dichloropropionylamido)phenylsulfonyl]-N'-(4-methoxy-6-methyl-1,3,5-triazin-2-yl)urea,
N-(2-chloroacetylamidophenylsulfonyl)-N'-(4-methoxy-6-methyl-1,3,5-triazin-2-yl)urea,
N-(2-methylsulfonamidophenylsulfonyl)-N'-(4-methoxy-6-methyl-1,3,5-triazin-2-yl)urea,
N-(2-bromoacetamidophenylsulfonyl)-N'-(4-methoxy-6-methyl-1,3,5-triazin-2-yl)urea,
N-(2-dichloroacetamidophenylsulfonyl)-N'-(4-methoxy-6-methyl-1,3,5-triazin-2-yl)urea,
N-(2-methoxyacetamidophenylsulfonyl)-N'-(4-methoxy-6-methyl-1,3,5-triazin-2-yl)urea,
N-[2-chloroacetylamido-6-chlorophenylsulfonyl]-N'-(4-methoxy-6-methyl-1,3,5-triazin-2-yl)urea,
N-[2-(4'-chlorobutyrylamido)phenylsulfonyl]-N'-(4-methoxy-6-methyl-1,3,5-triazin-2-yl)urea,
N-(2-methoxyoxalylamidophenylsulfonyl)-N'-(4-methoxy-6-methyl-1,3,5-triazin-2-yl)urea
N-(2-ethoxyoxalylamidophenylsulfonyl)-N'-(4-methoxy-6-methyl-1,3,5-triazin-2-yl)urea,
N-[2-(4'-chlorobutyrylamido)phenylsulfonyl]-N'-(4,6-dimethoxy-1,3,5-triazin-2-yl)urea,
N-[2-(4'-chlorobutyrylamido)-6-chlorophenylsulfonyl]-N'-(4-methoxy-6-methyl-1,3,5-triazin-2-yl)urea,
N-[2-(2'-piperidonyl)phenylsulfonyl]-N'-(4-methoxy-6-methyl-1,3,5-triazin-2-yl)urea,
N-(2-trifluoroacetamido-6-chlorophenylsulfonyl)-N'-(4-methoxy-6-methyl-1,3,5-triazin-2-yl)urea,
N-(2-bromoacetamido-6-chlorophenylsulfonyl)-N'-(4-methoxy-6-methyl-1,3,5-triazin-2-yl)urea.

The preparation of the compounds of the formula I is carried out in an inert organic solvent.

A first process for the preparation of the compounds of formula I comprises reacting a phenylsulfonamide of the formula II

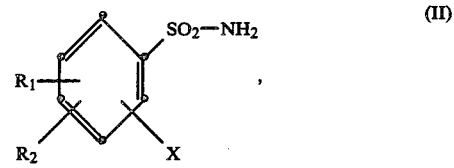

wherein X, $R_1$ and $R_2$ are as defined for formula I, with a N-triazinylcarbamate of the formula III

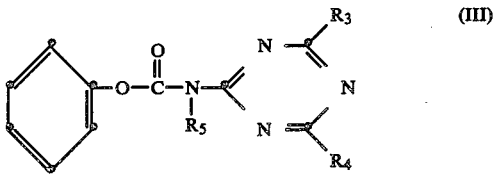

wherein $R_3$, $R_4$ and $R_5$ are as defined for formula I, and the phenyl radical can be unsubstituted or substituted, in the presence of a base.

A second process for the preparation of compounds of formula I comprises reacting a phenylsulfonylisocyanate or phenylsulfonylisothiocyanate of the formula IV

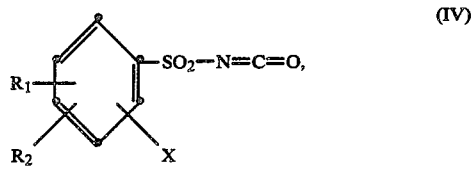

wherein X, $R_1$ $R_2$ are as defined for formula I, with an amine of the formula V

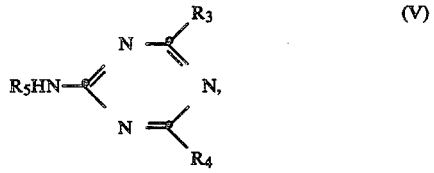

wherein $R_3$, $R_4$ and $R_5$ are as defined for formula I, optionally in the presence of a base.

A further process for the preparation of the compounds of formula I wherein $R_5$ is hydrogen, comprises reacting a sulfonamide of the formula II above with an isocyanate or isothiocyanate of the formula VI

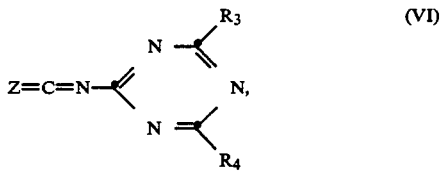

wherein $R_3$, $R_4$ and $Z$ are as defined for formula I, optionally in the presence of a base.

Finally, the compounds of the formula I can also be prepared by reacting an N-phenylsulfonylcarbamate of the formula VII

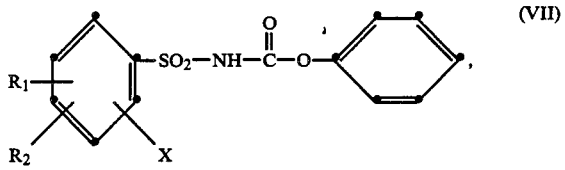

wherein X, $R_1$, $R_2$ and m are as defined for formula I and the phenoxy radical can be unsubstituted or substituted, with an amine of the formula V above.

If desired, the ureas of the formula I can be converted into addition salts by reaction with amines, alkali metal hydroxides or alkaline earth metal hydroxides or with quaternary ammonium bases, for example by reacting them with an equimolar amount of a base and removing the solvent by evaporation.

The compounds of formula II employed as intermediates are novel and have been sepcially developed for synthesising the compounds of formula I. These intermediates also constitute a further object of this invention.

The starting materials for obtaining the compounds of the formulae II, III, V and VI are known or they can be prepared by known methods.

The phenylsulfonylisocyanates of the formula IV can obtained by phosgenating the sulfonamides of the formula II, in the presence of butylisocyanate, in a chlorinated hydrocarbon as solvent, at reflux temperature. Similar reactions are described in "Newer Methods of Preparative Organic Chemistry", Vol. VI, 223–241, Academic Press, New York and London.

The isothiocyanates of the formula IV are obtained by treating the phenylsulfonamides of formula II with carbon disulfide and potassium hydroxide and by subsequent phosgenation of the dipotassium salt. Such processes are described in Arch. Pharm. 299, 174 (1966).

The N-phenylsulfonylcarbamates of the formula VII are obtained by reacting the phenylsulfonamides of the formula II with diphenyl carbonate in the presence of a base. Similar processes are described in Japanese Patent Specification No. 61 169.

Isocyanates of the formula VI can be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

It is convenient to carry out the reactions for obtaining compounds of formula I in aprotic inert organic solvents such as methylene chloride, tetrahydrofuran, acetonitrile, dioxan or toluene.

The reaction temperatures are preferably in the range from $-20°$ to $+120°$ C. The reactions are normally slightly exothermic and can be carried out at room temperature. To shorten the reaction time or also to initiate the reaction it is expedient to heat the reaction mixture briefly to boiling point. The reaction time can also be shortened by addition of a few drops of a base as catalyst.

The compounds of formula I are stable compounds and no protective measures are required for handling them.

When used at low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of this formula I are effective even when used at very low rates of application.

The compounds of the formula I have in addition pronounced growth-regulating, especially growth-inhibiting, properties. The growth of both monocots and dicots is inhibited.

Thus, for example, the compounds of formula I are able to inhibit selectively the growth of leguminosae which are frequently planted as cover crops in tropical regions, so that, while soil erosion between cultivated plants is prevented, the cover crops cannot compete with the cultivated plants.

Further, the compounds of formula I are suitable for preventing stored potatoes from seeding. During winter storage, potatoes often develop sprouts which result in shrinkage, weight loss, and rot. At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, as compositions, together with the adjuvants conventionally employed in formulation technology, and are therefore formulated in known manner to emulsifiable concentrates, directly sprayable or dilutable solutions, dilute emulsions, wettable powders, soluble powders, dusts, granulates, and also encapsulations in e.g. polymeric substances. As with the nature of the compositions, the methods of application such as spraying, scattering or pouring are chosen in accordance with the intended objectives and the prevailing circumstances.

The formulations, i.e. the compositions containing the compound of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts or higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of a naphthalenesulfonic acid/-formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and ,octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp. Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The herbicidal compositions usually contain 0.1 to 95%, preferably 0.1 to 80%, of a compound of the formula I, 1 to 99.9%, of a solid or liquid adjuvant, and 0 to 25%, preferably 0.1 to 25%, of a surfactant.

Preferred formulations are composed in particular of the following constituents (%=percentage by weight):

Emulsifiable concentrates
　active ingredient: 1 to 20%, preferably 5 to 10%
　surfactant: 5 to 30%, preferably 10 to 20%
　liquid carrier: 50 to 94%, preferably 70 to 85%

Dusts
　active ingredient: 0.1 to 10%, preferably 0.1 to 1%
　solid carrier: 99.9 to 90%, preferably 99.9to 99%

Suspension concentrates
　active ingredient: 5 to 75%, preferably 10 to 50%
　water: 94 to 25%, preferably 90 to 30%
　surfactant: 1 to 40%, preferably 2 to 30%

Wettable powders
　active ingredient: 0.5 to 90%, preferably 1 to 80%
　surfactant: 0.5 to 20%, preferably 1 to 15%
　solid carrier: 5 to 95%, preferably 15 to 90%

Granulates
　active ingredient: 0.5 to 30%, preferably 3 to 15%
　solid carrier: 99.5 to 70%, preferably 97 to 85%.

Whereas commercial products will be preferably formulated as concentrates, the end user will normally employ dilute formulations. The formulations can be diluted to a concentration as low as 0.001% The rates of application are normally from 0.01 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

The invention is illustrated by the following Examples.

EXAMPLE 1

Preparation of N-[2-(4'-chlorobutyrylamido)phenylsulfonyl]-N'-(4-methoxy-6-methyl-1,3,5-triazin-2-yl)urea

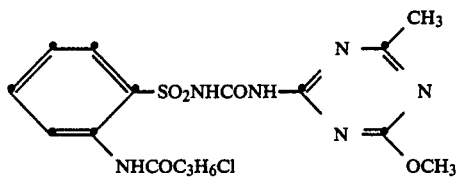

(a) 2-(4'-Chlorobutyrylamido)benzenesulfonamide

With stirring, a solution of 15.5 g (0.11 mole) of 4-chlorobutyryl chloride in 50 ml of acetonitrile is added dropwise over 2 hours at room temperature to a solution of 17.2 g (0.1 mole) of 2-amino benzenesulfonamide, 200 ml of acetonitrile and 8.9 ml of pyridine. When the dropwise addition is complete, stirring is continued for 4 hours and the reaction solution is poured into a mixture of 2N hydrochloric acid/ice and extracted twice with ethyl acetate. The organic phase is washed with a saturated solution of sodium bicarbonate and with a saturated solution of sodium chloride, dried, treated with activated carbon, and concentrated. The residue is recrystallised from ethyl acetate/hexane, yielding 17.7 g (64% of theory) of 2-(4'-chlorobutyrylamido)benzenesulfonamide with a melting point of 127°–129° C.

(b) N-[2-(4'-Chlorobutyrylamido)phenylsulfonyl]-N'-(4-methoxy-6-methyl-1,3,5-triazin-2-yl)urea To a solution of 2.76 g (0.01 mole) of 2-(4'-chlorobutyrylamido)benzenesulfonamide in 30 ml of dioxan are added 3.3 ml of 1,8-diazabicyclo[5.4.0]undec-7-ene and 2.60 g (0.01 mole) of N-(4-methoxy-6-methyl-1,3,5-triazin-2-yl)phenylcarbamate and the mixture is stirred for 24 hours at 20°–25° C. The reaction mixture is then poured into a 2N hydrochloric acid/ice mixture and well stirred for 2 hours. The precipitate is isolated by filtration, washed with 1N hydrochloric acid and water, dried, and recrystallised from ethanol, yielding 2.6 g (59% of theory) of the title urea with a melting point of 144°–145° C.

The following compounds and intermediates are prepared in corresponding manner:

TABLE 1

| No. | X | $R_1$ | $R_2$ | $R_3$ | $R_4$ | Physical data (°C.) |
|---|---|---|---|---|---|---|
| 1.01 | NHCOCF$_3$ | H | H | CH$_3$ | OCH$_3$ | m.p. 198° Z |
| 1.02 | NHCOCCl$_2$CH$_3$ | H | H | CH$_3$ | OCH$_3$ | m.p. 140–143° |
| 1.03 | NHCOCH$_2$Cl | H | H | CH$_3$ | OCH$_3$ | m.p. 165° Z |
| 1.04 | NHSO$_2$CH$_3$ | H | H | CH$_3$ | OCH$_3$ | m.p. 154–155° |
| 1.05 | NHCOCH$_2$Br | H | H | CH$_3$ | OCH$_3$ | m.p. 151–152° (decomp.) |
| 1.06 | NHCOCHCl$_2$ | H | H | CH$_3$ | OCH$_3$ | m.p. 143° Z |
| 1.07 | NHCOCH$_2$OCH$_3$ | H | H | CH$_3$ | OCH$_3$ | m.p. 171–172° |
| 1.08 | NH—COC—CH$_2$ \| CH$_2$ \| CH$_3$ (cyclopropyl-methyl) | H | H | CH$_3$ | OCH$_3$ | m.p. 146–149° |
| 1.09 | NHCOC$_3$H$_6$Cl | H | H | CH$_3$ | OCH$_3$ | m.p. 144–145° |
| 1.10 | NHCOCOOH$_3$ | H | H | CH$_3$ | OCH$_3$ | m.p. 151° (decomp.) |
| 1.11 | NHCOCOOC$_2$H$_5$ | 6-Cl | H | CH$_3$ | OCH$_3$ | |
| 1.12 | NHCOCH$_2$OCH$_3$ | 6-Cl | H | CH$_3$ | OCH$_3$ | |
| 1.13 | NHCOCH$_2$Cl | 6-Cl | H | CH$_3$ | OCH$_3$ | |
| 1.14 | NHCOC—CH$_2$ \| CH$_2$ \| CH$_3$ | 6-Cl | H | CH$_3$ | OCH$_3$ | |
| 1.15 | NHCOCHCl$_2$ | 6-Cl | H | CH$_3$ | OCH$_3$ | |
| 1.16 | NHCOCF$_3$ | 6-Cl | H | CH$_3$ | OCH$_3$ | |
| 1.17 | NHCOCH$_2$Br | 6-Cl | H | CH$_3$ | OCH$_3$ | m.p. 139° (decomp.) |
| 1.18 | NHSO$_2$CH$_3$ | 6-Cl | H | CH$_3$ | OCH$_3$ | |
| 1.19 | NHCOCCl$_2$CH$_3$ | 6-Cl | H | OCH$_3$ | OCH$_3$ | |
| 1.20 | NHCOCH$_2$Cl | H | H | OCH$_3$ | OCH$_3$ | |
| 1.21 | NHCOCH$_2$Cl | H | H | OCH$_3$ | N(CH$_3$)$_2$ | |
| 1.22 | NHCOCH$_2$Cl | 6-Cl | H | OCH$_3$ | OCH$_3$ | |
| 1.23 | NHCOCH$_2$Cl | 6-Cl | H | OCH$_3$ | N(CH$_3$)$_2$ | |
| 1.24 | NHCOCH$_2$Br | H | H | OCH$_3$ | OCH$_3$ | |
| 1.25 | NHCOCH$_2$Br | 6-Cl | H | OCH$_3$ | OCH$_3$ | |
| 1.26 | NHCOCH$_2$Cl | 6-COOCH$_3$ | H | CH$_3$ | OCH$_3$ | |
| 1.27 | NHCOCH$_2$OCH$_3$ | 6-COOCH$_3$ | H | CH$_3$ | OCH$_3$ | |

TABLE 1-continued

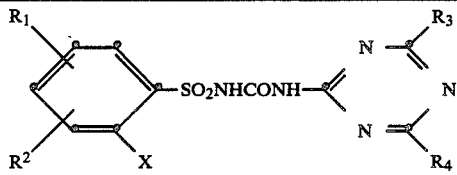

| No. | X | R₁ | R₂ | R₃ | R₄ | Physical data (°C.) |
|---|---|---|---|---|---|---|
| 1.28 | NHCONHC₂H₄Cl | H | H | CH₃ | OCH₃ | |
| 1.29 | NHCOOC₂H₄Cl | H | H | CH₃ | OCH₃ | |
| 1.30 | 2-pyrrolidon-1-yl | H | H | CH₃ | OCH₃ | |
| 1.31 | 2-pyrrolidon-1-yl | 6-Cl | H | CH₃ | OCH₃ | |
| 1.32 | 2-pyrrolidon-1-yl | 6-Cl | H | OCH₃ | N(CH₃)₂ | |
| 1.33 | 1,1-dioxo-2-isothiazolidinyl | H | H | CH₃ | OCH₃ | m.p. 212° (decomp.) |
| 1.34 | 1,1-dioxo-2-isothiazolidinyl | 6-Cl | H | CH₃ | OCH₃ | |
| 1.35 | 2-pyrrolidon-1-yl | 6-COOCH₃ | H | CH₃ | OCH₃ | |
| 1.36 | 2-piperidinon-1-yl | H | H | CH₃ | OCH₃ | |
| 1.37 | 1,3-oxazol-2-on-3-yl | H | H | CH₃ | OCH₃ | |
| 1.38 | —N(CH₃)CH₂CH=CH₂ | H | H | CH₃ | OCH₃ | |
| 1.39 | 2,5-pyrrolidindion-1-yl | H | H | CH₃ | OCH₃ | m.p. 202–203° (decomp.) |
| 1.40 | 2,5-pyrrolidindion-1-yl | 6-Cl | H | CH₃ | OCH₃ | |
| 1.41 | NHCOCOOC₂H₅ | H | H | CH₃ | OCH₃ | m.p. 119° (decomp.) |
| 1.42 | NHCH=C(COOC₂H₅)₂ | H | H | CH₃ | OCH₃ | m.p. 173–176° |
| 1.43 | NHCOCOOCH₃ | 6-Cl | H | CH₃ | OCH₃ | m.p. 147° (decomp.) |
| 1.44 | NHCHO | H | H | CH₃ | OCH₃ | m.p. 156° (decomp.) |
| 1.45 | N(CH₃)COOCH₃ | H | H | CH₃ | OCH₃ | |
| 1.46 | N(CH₃)COCH₃ | 6-Cl | H | CH₃ | OCH₃ | |
| 1.47 | N(cyclopropyl)SO₂CH₃ | H | H | CH₃ | OCH₃ | m.p. 178–180° |

TABLE 2

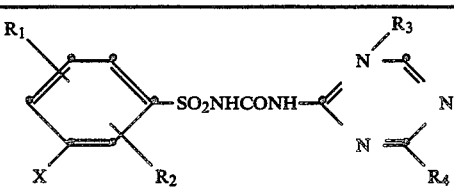

| No. | X | R₁ | R₂ | R₃ | R₄ | Physical data (°C.) |
|---|---|---|---|---|---|---|
| 2.01 | NH—CH=C(COOC₂H₅)₂ | H | H | CH₃ | OCH₃ | m.p. 182–184° (decomp.) |
| 2.02 | NH—CH=C(CN)COOC₂H₅ | H | H | CH₃ | OCH₃ | |
| 2.03 | NH—CH=C(COOCH₃)₂ | H | H | CH₃ | OCH₃ | |
| 2.04 | NH—C(CH₃)=CHCOCH₃ | H | H | CH₃ | OCH₃ | m.p. 163–166° (decomp.) |
| 2.05 | NH—C(CH₃)=CHCOCF₃ | H | H | CH₃ | OCH₃ | m.p. 184–186° (decomp.) |
| 2.06 | NH—C(CH₃)=CH—COOCH₃ | H | H | CH₃ | OCH₃ | m.p. 157–159° (decomp.) |
| 2.07 | 2-methoxycarbonylcyclopent-1-en-ylamino | H | H | CH₃ | OCH₃ | m.p. 155–157° (decomp.) |
| 2.08 | NHCHO | H | H | CH₃ | OCH₃ | m.p. 176° (decomp.) |
| 2.09 | NHCOC₃H₆Cl | H | H | CH₃ | OCH₃ | m.p. 112° (decomp.) |
| 2.10 | 2-pyrrolidon-1-yl | H | H | CH₃ | OCH₃ | |
| 2.11 | 1,1-dioxo-2-isothiazolidinyl | H | H | CH₃ | OCH₃ | m.p. 204° (decomp.) |
| 2.12 | 2-piperidinon-1-yl | H | H | CH₃ | OCH₃ | m.p. 181–182° (decomp.) |
| 2.13 | N(SO₂CH₃)₂ | H | H | CH₃ | OCH₃ | m.p. 185–190° (decomp.) |
| 2.14 | 2-pyrrolidon-1-yl | 6-Cl | H | CH₃ | OCH₃ | m.p. 150° (decomp.) |
| 2.15 | NHCOCF₃ | H | H | CH₃ | OCH₃ | m.p. 180–188° (decomp.) |

TABLE 3

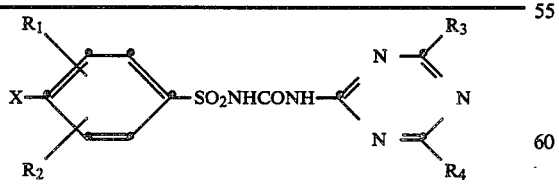

| No. | X | R₁ | R₂ | R₃ | R₄ | Physical data (°C.) |
|---|---|---|---|---|---|---|
| 3.01 | NHCH=C(COOC₂H₅)₂ | H | H | CH₃ | OCH₃ | |
| 3.02 | NHCH=C(CN)COOC₂H₅ | H | H | CH₃ | OCH₃ | |
| 3.03 | NHC(CH₃)=CHCOCH₃ | H | H | CH₃ | OCH₃ | |
| 3.04 | NHC(CH₃)=CHCOCF₃ | H | H | CH₃ | OCH₃ | |
| 3.05 | NHC(CH₃)=CHCOOCH₃ | H | H | CH₃ | OCH₃ | |
| 3.06 | 2-methoxycarbonyl-cyclopent-1-en-ylamino | H | H | CH₃ | OCH₃ | |
| 3.07 | NHCHO | H | H | CH₃ | OCH₃ | |

TABLE 3-continued

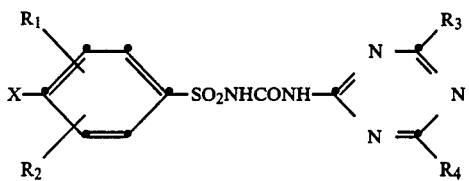

| No. | X | R₁ | R₂ | R₃ | R₄ | Physical data (°C.) |
|---|---|---|---|---|---|---|
| 3.08 | NHCOC₃H₆Cl | H | H | CH₃ | OCH₃ | m.p. 185° (decomp.) |
| 3.09 | pyrrolidon-1-yl | H | H | CH₃ | OCH₃ | m.p. 168° (decomp.) |

TABLE 4

Intermediates

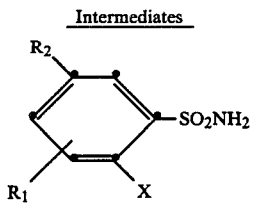

| No. | X | R₁ | R₂ | Physical data (°C.) |
|---|---|---|---|---|
| 4.01 | NHCOCF₃ | H | H | |
| 4.02 | NHCOCCl₂CH₃ | H | | |
| 4.03 | NHCOCH₂Cl | H | H | |
| 4.04 | NHSO₂CH₃ | H | H | |
| 4.05 | NHCOCH₂Br | H | H | |
| 4.06 | NHCOCHCl₂ | H | H | |
| 4.07 | NHCOCH₂OCH₃ | H | H | |
| 4.08 | NHCOC₃H₆Cl | H | H | m.p. 127-129° |
| 4.09 | NHCOCOOCH₃ | H | H | m.p. 202-203° |
| 4.10 | NHCOCOOC₂H₅ | H | H | m.p. 187° |
| 4.11 | NHCOCH₂OCH₃ | 6-Cl | H | |
| 4.12 | NHCOCH₂Cl | 6-Cl | H | m.p. 163-165° |
| 4.13 | NHCOCF₃ | 6-Cl | H | |
| 4.14 | NHCOCH₂Br | 6-Cl | H | |
| 4.15 | NHSO₂CH₃ | 6-Cl | H | m.p. 178° |
| 4.16 |  NHCOC—CH₂<br>   \| \|<br>   N—CH₂<br>   CH₃ | 6-Cl | H | |
| 4.17 | NHCOCH₂Cl | 6-COOCH₃ | H | |
| 4.18 | NHCOC₃H₆Cl | 6-COOCH₃ | H | |
| 4.19 | NHCOC₃H₆Cl | 6-Cl | H | m.p. 128-130 |
| 4.20 | NHCONHC₂H₄Cl | 6-Cl | H | |
| 4.21 | 1,1-dioxo-2-isothiazolidinyl | H | H | |
| 4.22 | N(CH₃)CH₂CH=CH₂ | H | H | |
| 4.23 | NHCOCOOCH₃ | 6-Cl | H | m.p. 201-202° |
| 4.24 | 2,5-pyrrolidindion-1-yl | H | H | m.p. 251° (decomp.) |
| 4.25 | 2,5-pyrrolidindion-1-yl | 6-Cl | H | |
| 4.26 | NHCHO | H | H | |

TABLE 5

Intermediates

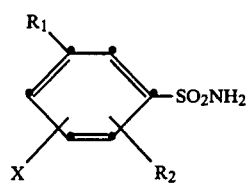

| No. | X | R₁ | R₂ | Physical data (°C.) |
|---|---|---|---|---|
| 5.01 | 3-NHCOC₃H₆Cl | H | H | 131° |
| 5.02 | 3-(2-pyrrolidon-1-yl) | H | H | 198-199° |
| 5.03 | 3-(1,1-dioxo-isothiazolidinyl) | H | H | m.p. 152° |
| 5.04 | 3-(2,5-pyrrolidion-1-yl) | H | H | |
| 5.05 | 3-NHCHO | H | H | |
| 5.06 | 3-NHCH=C(COOC₂H₅)₂ | H | H | m.p. 173-175° |
| 5.07 | 3-NHCH=C(CN)₂ | H | H | |
| 5.08 | 3-NHC(CH₃)=CHCOCH₃ | H | H | m.p. 159-161° |
| 5.09 | 3-NHC(CH₃)=CHCOCF₂ | H | H | m.p. 149-151° |
| 5.10 | 3-NHC(CH₃)=CH—COOCH₃ | H | H | m.p. 150-152° |
| 5.11 | 3-(2-methoxycarbonyl-cyclohex-1-en-yl-amino) | H | H | m.p. 180-182° |
| 5.12 | 3-N(SO₂CH₃)₂ | H | H | m.p. 203-206° |
| 5.13 | 3-(2-piperidon-1-yl) | H | H | |
| 5.20 | 4-NHCOC₃H₆Cl | H | H | m.p. 183° |
| 5.21 | 4-(2-pyrrolidon-1-yl) | H | H | m.p. 244-245° |
| 5.22 | 4-NHCHO | H | H | |
| 5.23 | 4-NHCH=C(COOC₂H₅)₂ | H | H | m.p. 152-154° |
| 5.24 | 4-NHC(CH₃)=CHCOCH₃ | H | H | |
| 5.25 | 4-NHC(CH₃)=CHCOCF₃ | H | H | |
| 5.26 | 4-NHC(CH₃)=CHCOOCH₃ | H | H | |
| 5.27 | 4-(2-methoxycarbonyl-cyclohex-1-en-ylamino) | | | |

TABLE 6

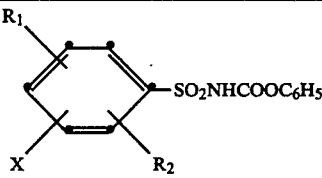

| No. | X | R₁ | R₂ | Physical data (°C.) |
|---|---|---|---|---|
| 6.01 | 3-(γ-pyrrolidon-1-yl) | H | H | |
| 6.02 | 3-(1,1-dioxo-isothiazolidinyl) | H | H | |
| 6.03 | 3-(2-piperidon-1-yl) | H | H | |

FORMULATION EXAMPLES

EXAMPLE 2

Formulation Examples for compounds of the formula I (percentages are by weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphahalenesulfonate | — | 6% | 6% |
| octylphenol polyethylene glycol ether (7-8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexane | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glycol ether (78 moles of ethylene oxide) | 3% |
| water | 91% |

BIOLOGICAL EXAMPLES

EXAMPLE 3

Preemergence herbicidal action

Plastic pots are filled with expanded vermiculite (density: 0.135 g/cm$^3$, water-absorbing capacity: 0.565 l/l. After the nonadsorptive vermiculite has been saturated with an aqueous emulsion in deionized water which contains the test compound in a concentration of 70.8 ppm, seeds of the following plants are sown on the surface: *Nasturtium officinalis, Agrostis tenuis, Stellaria media* and *Digitaria sanguinalis.* The pots are then kept in a climatic chamber at 20° C., an illumination of about 20 lux and a relative humidity of 70%. During the germinating phase of 4 to 6 days, the pots are dovered with lightpermeable material and watered with deionised water to increase the local humidity. After the 5th day, 0.5% of a commercial liquid fertiliser (Greenzit ®) is added to the water. The test is evaluated 12 days after sowing and the action on the plants is assessed according to the following rating:

1: plants have not emerged or are totally withered
2–3: very pronounced action
4–6: medium action
7–8: weak action
9: no action (as untreated controls).

The results are tabulated below.

Preemergence action:

Concentration of the test compound emulsion: 70.8 ppm

TABLE 7

| | Plant | | | |
|---|---|---|---|---|
| compound No. | Nasturtium officinalis | Agrostis tenuis | Stellaria media | Digitalis sanguinalis |
| 1.02 | 2 | 2 | 1 | 1 |
| 1.03 | 2 | 2 | 2 | 2 |
| 1.04 | 2 | 1 | 2 | 2 |
| 1.05 | 1 | 1 | 1 | 1 |
| 1.07 | 2 | 2 | 2 | 2 |
| 1.08 | 2 | 2 | 1 | 1 |
| 1.09 | 1 | 1 | 2 | 2 |
| 1.10 | 2 | 2 | 3 | 3 |
| 1.11 | 2 | 2 | 3 | 3 |
| 1.18 | 3 | 3 | 2 | 2 |
| 1.33 | 1 | 1 | 2 | 2 |
| 1.41 | 2 | 2 | 3 | 3 |
| 1.42 | 2 | 6 | 2 | 4 |
| 1.43 | 2 | 2 | 3 | 3 |
| 1.47 | 4 | 6 | 3 | 2 |
| 2.01 | 1 | 1 | 2 | 2 |
| 2.04 | 1 | 1 | 2 | 2 |
| 2.05 | 2 | 1 | 3 | 2 |
| 2.06 | 1 | 1 | 1 | 1 |
| 2.07 | 1 | 1 | 2 | 2 |
| 2.08 | 2 | 1 | 2 | 1 |
| 2.09 | 1 | 1 | 3 | 2 |
| 2.11 | 2 | 2 | 3 | 3 |
| 2.13 | 2 | 1 | 3 | 3 |
| 2.15 | 2 | 1 | 2 | 1 |
| 3.08 | 2 | 1 | 1 | 1 |

EXAMPLE 4

In another test the selective herbicidal activity in pre-and post-emergence application in wheat of the compounds 1.01, 1.04 and 1.06 was compared with that of compound N-(2-Aminophenylsulfonyl)-N'-(4-methoxy-6-methyl-1,3,5-triazin-2-yl) urea, known from U.S. Pat. No. 4,225,337, Col. 17, line 15 compound A.

Pre-emergence method

Seeds of plants (wheat and weeds) are put into pots in the greenhouse, so that about 20 plants will emerge per pot. Immediately afterwards the pots are sprayed with an aqueous emulsion, of the compounds to be tested in concentration that amounts to a field application of test-substance corresponding to 0.25 kg per hectare. The pots are then kept in the greenhouse under optimal conditions for plant growth, i.e. 20° C., 50 to 70% relative humidity, regular watering. The test was evaluated after 3 weeks and the state of the plants was assessed on the basis of the above given 1-9 scale of values.

Post-emergence method

Wheat and the weeds are reared from seeds in pots in a greenhouse. The pots have 11 cm diameter and the seeds are so applied that about 20 plants will emerge per pot. When the young plants have reached the 4- to 6-leaf stage, they are sprayed with aqueous active substance emulsions (obtained from the 25% concentrate) in a rate of application that corresponds to 0.25 kg per hectare of test substance. The treated plants are then kept in the greenhouse at optimum conditions of light, watering, temperature (20° C.) and humidity 50-70% relative humidity). The evaluation of the test was made 15 days after the treatment. The state of the plants was examined and rated according to above given scale of values.

The results are resumed in the Table 8.

TABLE 8

| mode of application | pre-emergence | | | | post-emergence | | | |
|---|---|---|---|---|---|---|---|---|
| compound No. | 1.01 | 1.04 | 1.06 | A | 1.01 | 1.04 | 1.06 | A |
| Plant | | | | | | | | |
| wheat | 8 | 8 | 6 | 7 | 9 | 8 | 9 | 9 |
| Alopecurus myosuroides | 3 | 4 | 4 | 6 | 3 | 4 | 4 | 7 |
| Echinochloa crus galli | 1 | 2 | 2 | 2 | 2 | 3 | 3 | 2 |
| Chenopodium album | 3 | 2 | 2 | 3 | 3 | 3 | 3 | 4 |
| Ipomoea purpurea | 4 | 4 | 4 | 7 | 4 | 4 | 4 | 8 |
| Sinapis alba | 2 | 2 | 2 | 2 | 2 | 2 | 2 | 2 |
| Galium apanne | 3 | 3 | 2 | 2 | 3 | 3 | 3 | 7 |

EXAMPLE 5

Inhibition of sprouting in stored potatoes

A number or commercially available potatoes of the "Urgenta" variety, without sprouts, are washed and dried. The potatoes are then immersed in emulsions of the compounds to be tested in different concentrations, placed on filter paper in plastic dishes, and kept in the dark at 14°–21° C. and 50% relative humidity. Evaluation is made 34 days after application.

The percentage weight loss of the tubers and the weight of the sprouts compared with untreated controls are simultaneously determined.

In the test, the compounds of the tables 1 to 3 inhibit sprouting completely. At the same time, the weight loss of the potatoes is less than 10% of that of the controls.

EXAMPLE 6

Growth inhibition of tropical cover crops

The test plants (centrosema plumieri and centrosema pubescens) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of tables 1 to 3 is observed (less than 20% of the new growth of untreated control plants), without damage being caused to the test plants.

What is claimed is:

1. An N-phenylsulfonyl-N'-triazinylurea of the formula

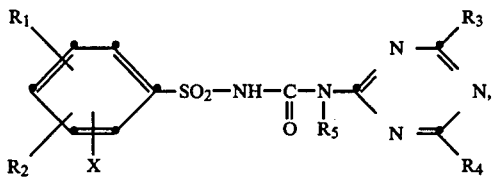

wherein
$R_1$ is hydrogen, halogen, or $COOC_1$-$C_5$alkyl
$R_2$ is hydrogen, or halogen,
$R_3$ is $C_1$-$C_3$alkyl, $C_1$-$C_3$haloalkyl, $C_1$-$C_3$alkoxy, $C_1$-$C_3$haloalkoxy,
$R_4$ is hydrogen, halogen, $C_1$-$C_3$ alkyl, $C_1$-$C_3$haloalkyl, $C_1$-$C_3$alkoxy, $C_1$-$C_3$haloalkoxy, $C_2$-$C_4$alkoxyalkyl, amino, $C_1$-$C_3$alkylamino or di-$C_1$-$C_3$alkylamino,
$R_5$ is hydrogen or methyl
X is $-NR_6R_7$, $-N(SO_2CH_3)_2$ or

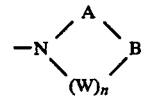

wherein
A is $-CO-$ or $-SO_2-$,
B is $C_1$-$C_4$ alkylene or $C_2$-$C_4$alkenylene,
W is $-CO-$ or $-SO_2-$,
n is 0 or 1,
$R_6$ is unsubstituted $C_3$-$C_7$cycloalkyl or $C_5$-$C_7$cycloalkenyl, or $C_2$-$C_6$alkenyl substituted by halogen, cyano or $-COOR_{11}$; or $R_6$ is $-COR_8$ or $-COCOC_1$-$C_3$alkyl,
$R_7$ is hydrogen, $C_1$-$C_4$alkyl, $C_3$-$C_7$cycloalkyl or $-SO_2CH_3$,
$R_8$ is hydrogen, $C_3$-$C_7$cycloalkyl, $C_1$-$C_5$haloalkyl or $C_2$-$C_5$alkoxyalkyl and
$R_{11}$ is hydrogen, $C_1$-$C_5$haloalkyl, $C_2$-$C_5$alkoxyalkyl, $C_2$-$C_6$alkenyl, $C_2$-$C_4$haloalkenyl or $C_2$-$C_4$alkynyl.

2. A N-phenylsulfonyl-N'-triazinylurea of claim 1, wherein $R_3$ and $R_4$ together contain not more than 4 carbon atoms.

3. An N-phenylsulfonyl-N'-triazinylurea of claim 1, wherein
$R_1$ is hydrogen or halogen,
$R_2$ is hydrogen,
$R_3$ is $C_1$-$C_3$alkyl or $C_1$-$C_3$alkoxy,
$R_4$ has the same meaning as $R_3$ or is $C_1$-$C_4$alkyl or dialkylamino,
$R_5$ is hydrogen or methyl,
X is $NR_6R_7$ or

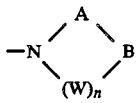

wherein
$R_6$ is unsubstituted $C_3$-$C_7$cycloalkyl or $C_5$-$C_7$cycloalkenyl, or $C_2$-$C_6$alkenyl substituted by halogen, cyano, —CO—$C_1$-$C_5$alkyl or —COO$C_1$-$C_5$alkyl, or is —CO—$C_1$-$C_5$haloakyl, —CO—C-2-$C_{10}$alkoxyalkyl, —CO—$C_3$-$C_7$cycloalkyl, or —COCOO—$C_1$-$C_5$alkyl,
$R_7$ is hydrogen, $C_1$-$C_4$alkyl, $C_3$-$C_7$cycloalkyl or —$SO_2CH_3$ and

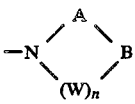

is pyrrolidine-2-on-1-yl, 1,1-dioxo-isothiazolidine-2-yl, piperidine-2-on-1-yl or pyrrolidine-2,5-dion-1-yl.

4. An N-phenylsulfonyl-n'-triazinyl-urea of claim 1, wherein
$R_1$ is hydrogen or halogen,
$R_2$ is hydrogen,
$R_3$ is $C_1$-$C_3$alkyl or $C_1$-$C_3$alkoxy,
$R_4$ is $C_1$-$C_3$alkyl, $C_1$-$C_3$alkoxy or di($C_1$-$C_3$)alkylamine,
$R_5$ is hydrogen,
X is —NH—$C_3$-$C_7$cycloalkyl or —NH—$C_5$-$C_7$cycloalkenyl, unsubstituted or —NH$C_2$-$C_5$alkenyl substituted by halogen, cyano, —COO—$C_1$-$C_5$alkyl, or it is —NHCHO, —NHCO—$C_1$-$C_5$haloalkyl, —NHCOO—$C_1$-$C_5$haloalkyl, —NHCOCOO—$C_1$-$C_5$alkyl, —N($SO_2$—$CH_3$)$_2$; or is pyrrolidine-2-on-1-yl, 1,1-dioxo-isothiazilidine-2-yl, piperidine-2-on-1-yl, or pyrrolidine-2,5-dion-1-yl.

5. N-[2-(2', 2'-Dichloropropionylamido)phenylsulfonyl-N'-(4-methoxy-6-methyl-1,3,5-triazin-2-yl)urea according to claim 1.

6. N-(2-Dichloroacetylamidophenylsulfonyl)]-N'-(4-methoxy-6-methyl-1,3,5-triazin-2-yl)urea according to claim 1.

7. N-(2-Bromoacetamidophenylsulfonyl)-N'-(4-methoxy-6-methyl-1,3,5-triazin-2-yl)urea according to claim 1.

8. N-[2-Chloroacetamido-6-chlorophenylsulfonyl]-N'-(4-methoxy-6-methyl-1,3,5-triazin-2-yl)urea according to claim 1.

9. N-[2-(4'-Chlorobutyrylamido)phenylsulfonyl]-N'-(4-methoxy-6-methyl-1,3,5-triazin-2-yl)urea according to claim 1.

10. N-(2-Methoxyoxalylamidophenylsulfonyl)-N'-(4-methoxy-6-methyl-1,3,5-triazin-2-yl)urea according to claim 1.

11. N-(2-Methoxyoxalylamido-6-chlorophenylsulfonyl)-N'-(4-methoxy-6-methyl-1,3,5-triazin-2-yl)urea according to claim 1.

12. A herbicidal and plant growth inhibiting composition which comprises an effective amount of a N-phenylsulfonyl-N'-triazinylurea of claim 1, together with carriers or other adjuvants.

13. A method of selectively controlling weeds pre- and post-emergence in crops of useful plants, which comprises treating the crops or the area where the crop is grown with an effective amount of a N-phenylsulfonyl-N'-triazinylurea of claim 1.

14. A method of selectively controlling weeds in pre- and post-emergence in crops of cereals, cotton, soybeans, maize and rice which comprises treating the crops or the area where the crop is grown with an effective amount of a N-phenylsulfonyl-N'-triazinylurea of claim 1.

* * * * *